United States Patent
Sezginer et al.

(10) Patent No.: US 9,494,535 B2
(45) Date of Patent: Nov. 15, 2016

(54) SCATTEROMETRY-BASED IMAGING AND CRITICAL DIMENSION METROLOGY

(71) Applicant: KLA-Tencor Corporation, Milpitas, CA (US)

(72) Inventors: Abdurrahman Sezginer, Monte Sereno, CA (US); John Hench, Los Gatos, CA (US); Michael S. Bakeman, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 24 days.

(21) Appl. No.: 14/690,442

(22) Filed: Apr. 19, 2015

(65) Prior Publication Data

US 2015/0300965 A1    Oct. 22, 2015

Related U.S. Application Data

(60) Provisional application No. 61/982,183, filed on Apr. 21, 2014, provisional application No. 61/982,326, filed on Apr. 22, 2014.

(51) Int. Cl.
*G01N 23/201* (2006.01)
*H01L 21/66* (2006.01)

(52) U.S. Cl.
CPC ....... *G01N 23/201* (2013.01); *G01N 2223/611* (2013.01); *G01N 2223/645* (2013.01); *H01L 22/12* (2013.01)

(58) Field of Classification Search
USPC ............................ 378/86, 87, 88, 89, 70, 71
See application file for complete search history.

(56) References Cited

U.S. PATENT DOCUMENTS

| | | |
|---|---|---|
| 6,349,128 B1 | 2/2002 | Nelson |
| 2003/0058443 A1 | 3/2003 | Xu et al. |
| 2003/0179365 A1 | 9/2003 | Koops et al. |
| 2011/0043791 A1 | 2/2011 | Smilde et al. |
| 2013/0027688 A1 | 1/2013 | Garcia Da Fonseca et al. |
| 2015/0117610 A1* | 4/2015 | Veldman ............. G03F 7/70633 378/71 |

OTHER PUBLICATIONS

International Search Report mailed on Jul. 28, 2015, for PCT Application No. PCT/US2015/026837 filed on Apr. 21, 2015 by KLA-Tencor Corporation, 4 pages.

* cited by examiner

*Primary Examiner* — Kiet T Nguyen
(74) *Attorney, Agent, or Firm* — Spano Law Group; Joseph S. Spano

(57) ABSTRACT

Methods and systems for performing measurements of semiconductor structures and materials based on scatterometry measurement data are presented. Scatterometry measurement data is used to generate an image of a material property of a measured structure based on the measured intensities of the detected diffraction orders. In some examples, a value of a parameter of interest is determined directly from the map of the material property of the measurement target. In some other examples, the image is compared to structural characteristics estimated by a geometric, model-based parametric inversion of the same measurement data. Discrepancies are used to update the geometric model of the measured structure and improve measurement performance. This enables a metrology system to converge on an accurate parametric measurement model when there are significant deviations between the actual shape of a manufactured structure subject to model-based measurement and the modeled shape of the structure.

25 Claims, 7 Drawing Sheets

SCATTEROMETRY-BASED IMAGING AND CRITICAL DIMENSION METROLOGY

CROSS REFERENCE TO RELATED APPLICATION

The present application for patent claims priority under 35 U.S.C. §119 from U.S. provisional patent application Ser. No. 61/982,183, entitled "X-Ray Imaging of Semiconductor Devices," filed Apr. 21, 2014, and from U.S. provisional patent application Ser. No. 61/982,326, entitled "X-Ray Imaging of Semiconductor Devices," filed Apr. 22, 2014, the subject matter of each is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of metrology based techniques including scatterometry and reflectometry implementations and associated analysis algorithms are commonly used to characterize critical dimensions, film thicknesses, composition and other parameters of nanoscale structures.

Traditionally, scatterometry measurements are performed on targets consisting of thin films and/or repeated periodic structures. During device fabrication, these films and periodic structures typically represent the actual device geometry and material structure or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. Optical metrology tools utilizing infrared to visible light can penetrate many layers of translucent materials, but longer wavelengths that provide good depth of penetration do not provide sufficient sensitivity to small anomalies. In addition, the increasing number of parameters required to characterize complex structures (e.g., FinFETs), leads to increasing parameter correlation. As a result, the parameters characterizing the target often cannot be reliably decoupled with available measurements.

In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response to these challenges, more complex optical metrology tools have been developed. For example, tools with multiple angles of illumination, shorter illumination wavelengths, broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Atomic force microscopes (AFM) and scanning-tunneling microscopes (STM) are able to achieve atomic resolution, but they can only probe the surface of the specimen. In addition, AFM and STM microscopes require long scanning times.

Scanning electron microscopes (SEM) achieve intermediate resolution levels, but are unable to penetrate structures to sufficient depth. Thus, high-aspect ratio holes are not characterized well. In addition, the required charging of the specimen has an adverse effect on imaging performance.

Transmission electron microscopes (TEM) achieve high resolution levels and are able to probe arbitrary depths, but TEM requires destructive sectioning of the specimen.

Small-Angle X-ray Scattering (SAXS) techniques have been shown to provide sufficient resolution and depth of penetration. Model-based interpretation of SAXS data assumes a representative model of the geometry and optical properties of the specimen. However, the measurement model has limited degrees of freedom; typically much less than the degrees of freedom of the measured data. If the actual sample is not accurately described by the measurement model, the resulting solution to the model based optimization does not provide any information concerning the source of the model mismatch. This makes it very difficult to develop a measurement model that properly characterizes a specimen unless the structure of the specimen is well-known a priori. This up-front knowledge of the specimen is often unavailable during process development Future metrology applications present challenges for metrology due to increasingly small resolution requirements, multi-parameter correlation, increasingly complex geometric structures, and increasing use of opaque materials. Thus, methods and systems for improved CD measurements are desired.

SUMMARY

Methods and systems for performing measurements of semiconductor structures and materials based on scatterometry measurement data are presented. Such systems are employed to measure structural and material characteristics (e.g., material composition, dimensional characteristics of structures, etc.) associated with different semiconductor fabrication processes.

More specifically, scatterometry measurement data is used to generate an image of a measured structure based on the measured intensities of the detected diffraction orders. In some examples, the image is compared to structural characteristics estimated by a geometric, model-based parametric inversion of the same scatterometry measurement data. Discrepancies are used to update the geometric model of the measured structure and improve measurement performance. The ability to converge on an accurate parametric measurement model is particularly important when measuring integrated circuits to control, monitor, and trouble-shoot their manufacturing process.

In one aspect, a computing system is configured to generate an model of a material property of a measured structure and resolve an image of the measured structure by performing a fitting analysis of scatterometry measurement data with the model. The model that describes the geometry and material parameters of the structure under measurement is a free-form model that does not include a preconceived geometry and material distribution. In some embodiments, the model includes many small voxels (volumetric elements) that each have an independently adjustable material parameter value (e.g., electron density, absorptivity, or complex refractive index). In some other embodiments, the material properties are piecewise constant. The properties associated with each different material are determined a priori. The boundaries between different materials are free-form surfaces, and these surfaces can be determined by the level set algorithm.

In a further aspect, the same scatterometry data acquired for CD metrology is used to calculate an image of the sample. In some examples, the image is a two dimensional (2-D) map of electron density, absorptivity, complex index of refraction, or a combination of these material characteristics. In some examples, the image is a three dimensional (3-D) map of electron density, absorptivity, complex index of refraction, or a combination of these material characteristics. The map is generated using relatively few physical constraints. The resulting map is generally unsuitable for measuring CD because it lacks sufficient resolution. However, the map is useful for debugging the wafer process when the sample geometry or materials deviate outside the range of expected values contemplated by the geometric model employed for CD measurement. In one example, the differences between the map and a rendering of the structure predicted by the geometric model according to its measured parameters are used to update the geometric model and improve its measurement performance.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
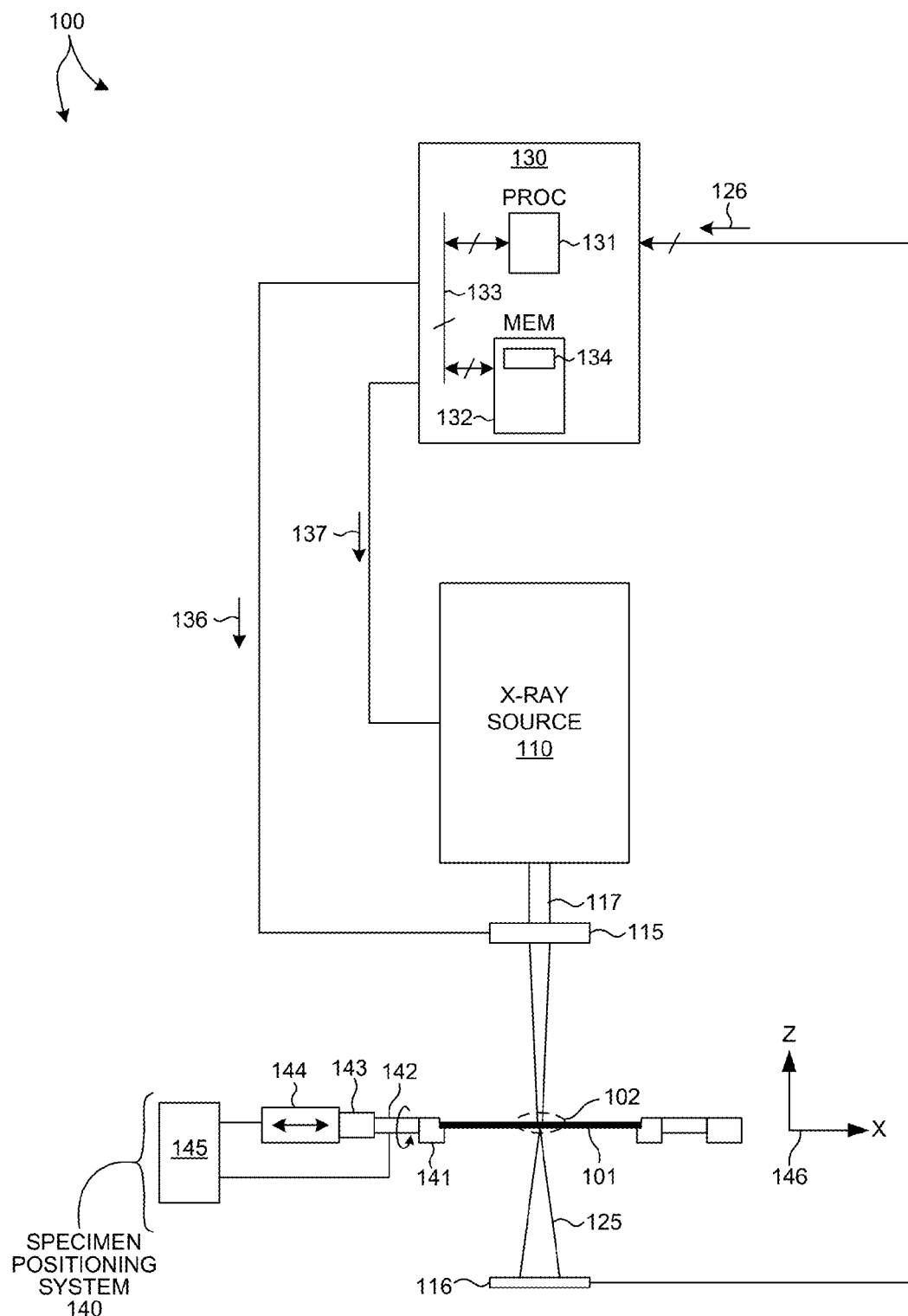
FIG. 1 is a diagram illustrative of a metrology system 100 configured to perform x-ray scatterometry measurements in accordance with the methods described herein.

Reference will now be made in detail to background examples and some embodiments of the invention, examples of which are illustrated in the accompanying drawings.

Methods and systems for performing measurements of semiconductor structures and materials based on scatterometry measurement data are presented. Such systems are employed to measure structural and material characteristics (e.g., material composition, dimensional characteristics of structures, etc.) associated with different semiconductor fabrication processes.

More specifically, scatterometry measurement data is used to generate an image of a measured structure based on the measured intensities of the detected diffraction orders. In some examples, the image is compared to structural characteristics estimated by a geometric, model-based parametric inversion of the same scatterometry measurement data. Discrepancies are used to update the geometric model of the measured structure and improve measurement performance. The ability to converge on an accurate parametric measurement model is particularly important when measuring integrated circuits to control, monitor, and trouble-shoot their manufacturing process.

Geometric, model-based, parametric inversion is preferred for critical dimension (CD) metrology based on SAXS measurements. However, when the measured specimen deviates from the assumptions of the geometric model, a map of the specimen generated from the same SAXS measurement data is useful to identify and correct model errors.

The use of high brightness SAXS (in either grazing incidence or transmission incidence configurations) enables high flux x-ray radiation penetration into opaque areas of the target. Examples of measureable geometric parameters using SAXS includes pore size, pore density, line edge roughness, line width roughness, side wall angle, profile, critical dimension, overlay, edge placement error, and pitch. Examples of measureable material parameters include electron density, elemental identification and composition. In some examples, SAXS enables the measurement of features smaller than 10 nm as well as advanced semiconductor structures such as spin-transfer-torque MRAM where measurements of geometrical parameters and material parameters are needed.

A SAXS measurement involves illuminating a sample with an X-ray beam and detecting the intensities of the resulting diffraction orders for multiple angles of incidence relative to the sample, multiple wavelengths, or both. CD metrology based on SAXS involves determining the dimensions of the sample from the measurements by regression. Regression uses a pre-determined geometric model with a few (on the order of ten) adjustable parameters. This reduces the uncertainty and increases the speed of the CD measurement, but also limits the set of possible shapes contemplated by the model. During manufacture, or particularly during process development, a specimen may fall outside this limited set of possible shapes. For example, a line may be under-cut when the model does not include that possibility. In this case, the model will fail to capture this geometric feature. In addition, the measurement will provide no indication of the particular source of this failure.

In one aspect, the same scatterometry data acquired for CD metrology is used to calculate an image of the sample. In some examples, the image is a two dimensional (2-D) map of electron density, absorptivity, complex index of refraction, or a combination of these material characteristics. In some examples, the image is a three dimensional (3-D) map of electron density, absorptivity, complex index of refraction, or a combination of these material characteristics. The map is generated using relatively few physical constraints. In some examples, one or more parameters of interest, such as critical dimension (CD), sidewall angle (SWA), overlay, edge placement error, pitch walk, etc., are estimated directly from the resulting map. In some other examples, the map is useful for debugging the wafer process when the sample geometry or materials deviate outside the range of expected values contemplated by a parametric structural model employed for model-based CD measurement. In one example, the differences between the map and a rendering of the structure predicted by the parametric structural model according to its measured parameters are used to update the parametric structural model and improve its measurement performance.

FIG. 1 illustrates an embodiment of a metrology tool 100 for measuring characteristics of a specimen in accordance with the exemplary methods presented herein. As shown in FIG. 1, the system 100 may be used to perform transmission SAXS measurements over an inspection area 102 of a specimen 101 disposed on a specimen positioning system 140. In some embodiments, the inspection area 102 has a spot size of fifty micrometers or less.

In the depicted embodiment, metrology tool 100 includes an x-ray illumination source 110 configured to generate x-ray radiation suitable for SAXS measurements. In some embodiments, the x-ray illumination system 110 is configured to generate wavelengths between 0.01 nanometers and 1 nanometer. X-ray illumination source 110 produces an x-ray beam 117 incident on inspection area 102 of specimen 101.

In general, any suitable high-brightness x-ray illumination source capable of generating high brightness x-rays at flux levels sufficient to enable high-throughput, inline metrology may be contemplated to supply x-ray illumination for SAXS measurements. In some embodiments, an x-ray source includes a tunable monochromator that enables the x-ray source to deliver x-ray radiation at different, selectable wavelengths.

In some embodiments, one or more x-ray sources emitting radiation with photon energy greater than 15 keV are employed. By way of non-limiting example, any of a particle accelerator source, a liquid anode source, a rotating anode source, a microfocus source, a microfocus rotating anode source, and an inverse Compton source may be employed as x-ray source 110. In one example, an inverse Compton source available from Lyncean Technologies, Inc., Palo Alto, Calif. (USA) may be contemplated. Inverse Compton sources have an additional advantage of being able to produce x-rays over a range of photon energies, thereby enabling the x-ray source to deliver x-ray radiation at different, selectable wavelengths.

Figure 2:
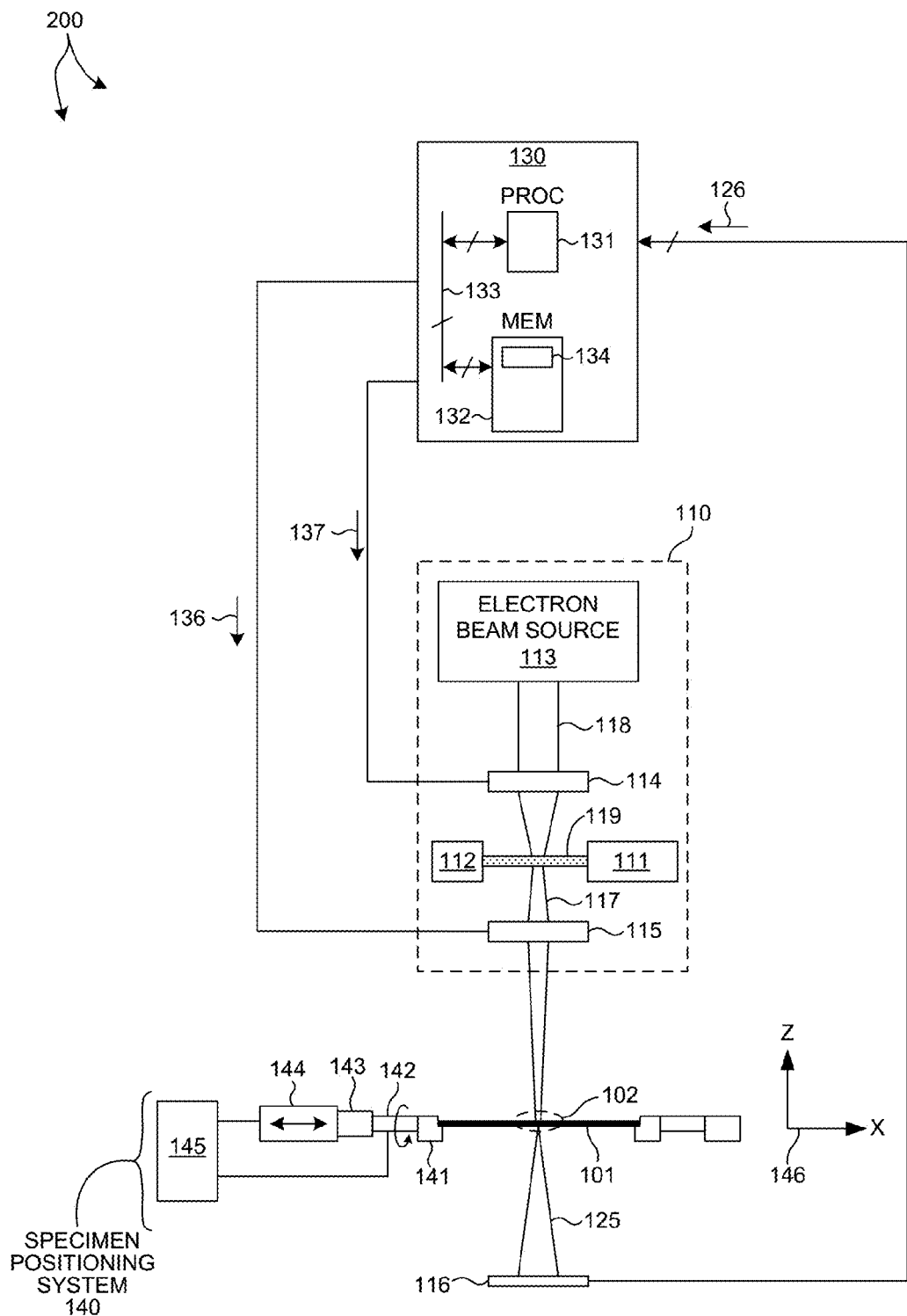
FIG. 2 is a diagram illustrative of a metrology system 200 in another embodiment configured to perform scatterometry measurements in accordance with the methods described herein.

Exemplary x-ray sources include electron beam sources configured to bombard solid or liquid targets to stimulate x-ray radiation. FIG. 2 depicts a metrology tool 200 for measuring characteristics of a specimen in accordance with the exemplary methods presented herein. Like numbered elements of metrology tool 100 and 200 are analogous. However, in the embodiment depicted in FIG. 2, x-ray illumination source 110 is a liquid metal based x-ray illumination system. A jet of liquid metal 119 is produced from a liquid metal container 111 and collected in a liquid metal collector 112. A liquid metal circulation system (not shown) returns liquid metal collected by collector 112 to liquid metal container 111. The jet of liquid metal 119 includes one or more elements. By way of non-limiting example, the jet of liquid metal 119 includes any of Aluminum, Gallium, Indium, Tin, Thallium, and Bismuth. In this manner, the jet of liquid metal 119 produces x-ray lines corresponding with its constituent elements. In one embodiment, the jet of liquid metal includes a Gallium and Indium alloy. In some embodiments, the x-ray illumination system 110 is configured to generate wavelengths between 0.01 nanometers and 1 nanometer. An electron beam source 113 (e.g., electron gun) produces a stream of electrons 118 that is directed by electron optics 114 to the jet of liquid metal 119. Suitable electron optics 114 includes electromagnets, permanent magnets, or a combination of electromagnets and permanent magnets for focusing the electron beam and directing the beam at the liquid metal jet. The coincidence of the jet of liquid metal 119 and the stream of electrons 118 produces an x-ray beam 117 incident on inspection area 102 of specimen 101.

In one embodiment, the incident x-ray beam 117 is at the Indium kα line of 24.2 keV. The x-ray beam is collimated down to less than one milliradian divergence using multilayer x-ray optics for transmission SAXS measurements.

In some embodiments, the x-ray scattering measurements described herein are achieved without using a screen located between the x-ray source and the specimen under measurement. In these embodiments, the measured intensities of the diffraction orders over a range of angles of incidence, multiple wavelengths, or a combination of both, provide sufficient information to resolve a distribution map (i.e., image) of the desired material property (e.g., complex refractive index, electron density, or absorptivity) of the measured structure. However, in some other examples, a pinhole or another aperture in located on an otherwise opaque screen that is located between the x-ray source and the specimen under measurement to improve collimation of the x-ray beam. The intensity of the diffraction pattern is measured for several positions of the aperture. In some other embodiments, a screen with a pseudo-random aperture pattern is used, and the diffraction pattern is measured for multiple screens. These approaches may also be contemplated to provide additional information to resolve the three-dimensional distribution of the desired material property of the measured structure.

Methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

As depicted in FIG. 1, x-ray optics 115 shape and direct incident x-ray beam 117 to specimen 101. In some examples, x-ray optics 115 include an x-ray monochromator to monochromatize the x-ray beam that is incident on the specimen 101. In one example, a crystal monochromator such as a Loxley-Tanner-Bowen monochromator is employed to monochromatize the beam of x-ray radiation. In some examples, x-ray optics 115 collimate or focus the x-ray beam 117 onto inspection area 102 of specimen 101 to less than 1 milliradian divergence using multilayer x-ray optics. In some embodiments, x-ray optics 115 includes one or more x-ray collimating mirrors, x-ray apertures, x-ray beam stops, refractive x-ray optics, diffractive optics such as zone plates, specular x-ray optics such as grazing incidence ellipsoidal mirrors, polycapillary optics such as hollow capillary x-ray waveguides, multilayer optics, or systems, or any combination thereof.

X-ray detector 116 collects x-ray radiation 125 scattered from specimen 101 and generates an output signal 126 indicative of properties of specimen 101 that are sensitive to the incident x-ray radiation in accordance with a SAXS measurement modality. In some embodiments, scattered x-rays 125 are collected by x-ray detector 116 while specimen positioning system 140 locates and orients specimen 101 to produce angularly resolved scattered x-rays. In some embodiments, the x-ray detector 116 is able to resolve one or more x-ray photon energies and produces signals for each x-ray energy component indicative of properties of the specimen. In some embodiments, the x-ray detector 116 includes any of a CCD array, a microchannel plate, a photodiode array, a microstrip proportional counter, a gas filled proportional counter, a scintillator, or a fluorescent material. In some embodiments, the x-ray detector 116 includes a single photon counting detector that detects the position and number of detected photons.

In some embodiments, x-ray detector 116 is maintained in the same atmospheric environment as specimen 101 (e.g., gas purge environment). However, in some embodiments, the distance between specimen 101 and x-ray detector 116 is lengthy (e.g., greater than one meter). In these embodiments, environmental disturbances (e.g., air turbulence) contribute noise to the detected signals. Hence in some embodiments, one or more of the x-ray detectors is maintained in a localized, vacuum environment separated from the specimen (e.g., specimen 101) by a vacuum window.

Figure 4:
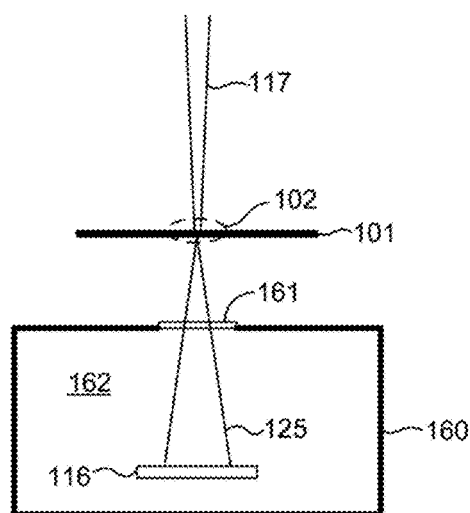
FIG. 4 is a diagram illustrative of a x-ray detector 116 of metrology systems 100, 200, and 300 contained in a vacuum environment 162 separate from specimen 101.

FIG. 4 is a diagram illustrative of a vacuum chamber 160 containing x-ray detector 116 in one embodiment. In a preferred embodiment, vacuum chamber 160 includes a substantial portion of the path between specimen 101 and x-ray detector 116. An opening of vacuum chamber 160 is covered by vacuum window 161. Vacuum window 161 may be constructed of any suitable material that is substantially transparent to x-ray radiation (e.g., Beryllium). Scattered x-ray radiation 125 passes through vacuum window 161, enters vacuum chamber 160 and is incident on x-ray detector 116. A suitable vacuum environment 162 is maintained within vacuum chamber 160 to minimize disturbances to scattered x-ray radiation 125.

Figure 3:
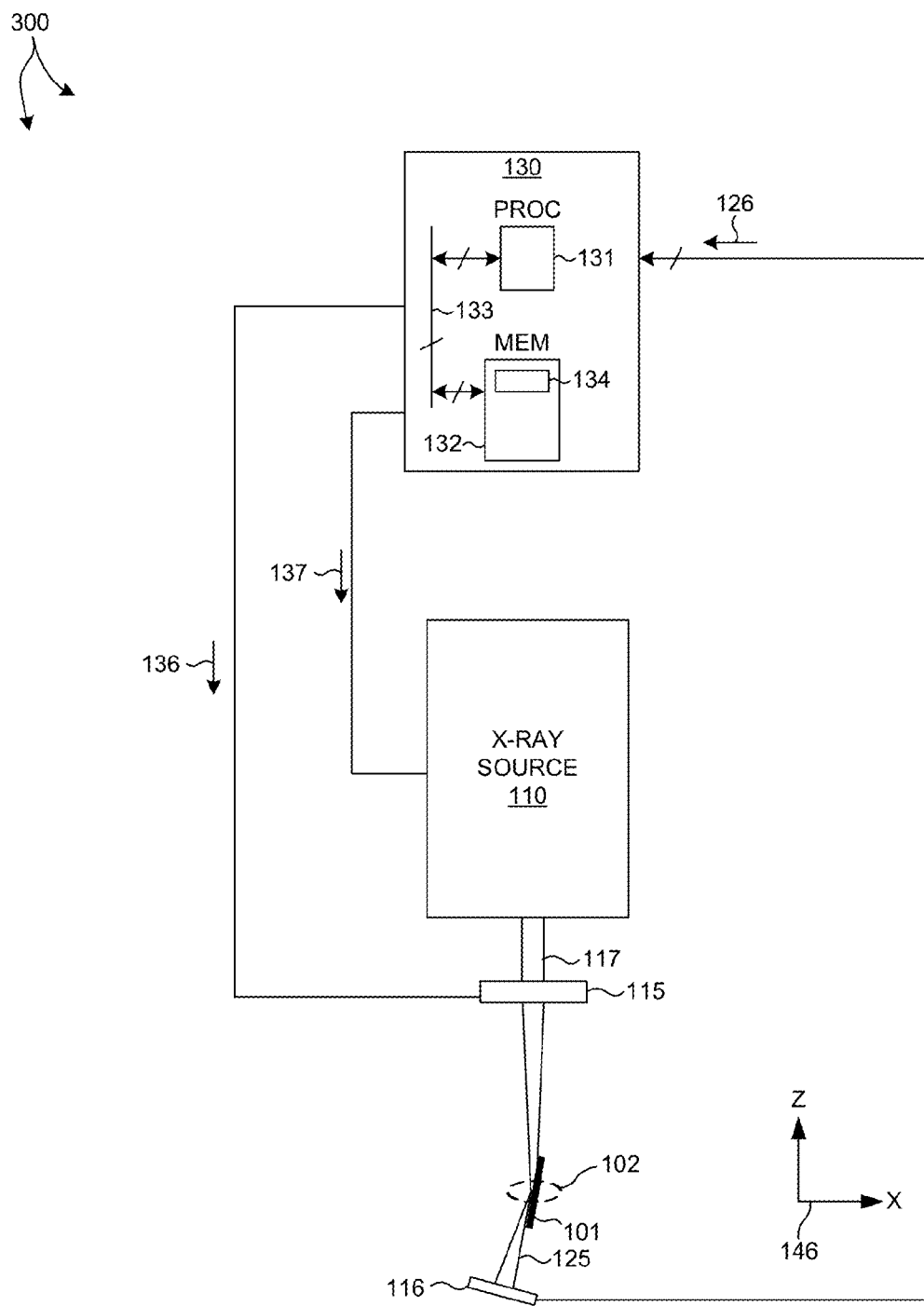
FIG. 3 is a diagram illustrative of a metrology system 300 in another embodiment configured to perform grazing incidence scatterometry measurements in accordance with the methods described herein.

FIG. 3 illustrates an x-ray metrology system 300 for performing semiconductor metrology measurements in accordance with the methods described herein. As illustrated in FIG. 3, x-ray metrology system 300 includes similar, like numbered elements described with reference to FIGS. 1 and 2. However, x-ray metrology system 300 operates in a grazing incidence mode. More specifically, x-ray metrology system 300 is configured as a grazing incidence small-angle x-ray scattering (GISAXS) measurement system. Typical angles of incidence and collection are approximately one degree as measured from the surface of the specimen, or approximately eighty nine degrees from an axis normal to the surface of the specimen. X-ray metrology system 300 is configured such that x-rays scattered from the specimen are collected by a detector while a sample handler (not shown) positions the specimen. In addition, any other particles produced during the interaction such as photoelectrons, x-rays produced through fluorescence, or ions can be detected. Metrology systems configured to perform GISAXS measurements require a high brightness x-ray source to maintain sufficient brightness over the relatively large sample area illuminated at small angles. For this reason, a liquid metal jet x-ray source 110 described with reference to FIG. 2 is particularly well suited for GISAXS measurements.

By way of non-limiting example, the x-ray metrology systems 100 and 200 illustrated in FIGS. 1 and 2, respectively, are configured as transmission small angle x-ray scatterometers (TSAXS) and the x-ray metrology system 300 illustrated in FIG. 3 is configured as a grazing incidence small angle x-ray scatterometer (GISAXS). However, in general, an x-ray metrology system configured to perform scatterometry based measurements and generate images as described herein may employ any one or more of the following metrology techniques: transmission small angle x-ray scattering (TSAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), x-ray tomography, x-ray ellipsometry, and hard x-ray photoemission spectrometry (HXPS).

Metrology tool 100 also includes a computing system 130 employed to acquire signals 126 generated by SAXS detector 116 and determine properties of the specimen based at least in part on the acquired signals. As illustrated in FIG. 1, computing system 130 is communicatively coupled to SAXS detector 116.

In a further embodiment, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In one further aspect, metrology tool 100 includes a computing system (e.g., computing system 130) configured to implement beam control functionality as described herein. In the embodiment depicted in FIG. 1, computing system 130 is configured as a beam controller operable to control any of the illumination properties such as intensity, divergence, spot size, polarization, spectrum, and positioning of the incident SAXS illumination beam 117.

As illustrated in FIG. 1, computing system 130 is communicatively coupled to SAXS detector 116. Computing system 130 is configured to receive measurement data 126 from SAXS detector 116. In one example, measurement data 126 includes an indication of the measured SAXS response of the specimen (i.e., intensities of the diffraction orders). Based on the distribution of the measured SAXS response on the surface of detector 116, the location and area of incidence of SAXS illumination beam 117 on specimen 101 is determined by computing system 130. In one example, pattern recognition techniques are applied by computing system 130 to determine the location and area of incidence of SAXS illumination beam 117 on specimen 101 based on measurement data 126. In some examples, computing system 130 communicates command signal 137 to illumination optics 115 to select the desired illumination wavelength and redirect and reshape SAXS illumination beam 117 such that incident SAXS illumination beam 117 arrives at the desired location and angular orientation with respect to specimen 101. In some other examples, computing system 130 communicates a command signal to wafer positioning system 140 to position and orient specimen 101 such that incident SAXS illumination beam 117 arrives at the desired location and angular orientation with respect to specimen 101. In some other examples, computing system 130 communicates a command signal 137 to x-ray source 110 to select the desired illumination wavelength and redirect and reshape SAXS illumination beam 117 such that incident SAXS illumination beam 117 arrives at the desired location and angular orientation with respect to specimen 101.

In another aspect, SAXS measurements of a particular inspection area are performed at a number of different angles of incidence. In some embodiments, it is desirable to perform measurements at different angles of incidence described by rotations about the x and y axes indicated by coordinate system 146 depicted in FIG. 1. This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy. For example, in a normal orientation, SAXS is able to resolve the critical dimension of a feature, but is largely insensitive to sidewall angle and height of a feature. However, by collecting measurement data over a broad range of out of plane angular positions, the sidewall angle and height of a feature can be resolved.

As illustrated in FIG. 1, metrology tool 100 includes a specimen positioning system 140 configured to both align specimen 101 and orient specimen 101 over a large range of out of plane angular orientations with respect to the SAXS scatterometer. In other words, specimen positioning system 140 is configured to rotate specimen 101 over a large angular range about one or more axes of rotation aligned in-plane with the surface of specimen 101. In some embodiments, specimen positioning system 140 is configured to rotate specimen 101 within a range of at least 90 degrees about one or more axes of rotation aligned in-plane with the surface of specimen 101. In some embodiments, specimen positioning system is configured to rotate specimen 101 within a range of at least 60 degrees about one or more axes of rotation aligned in-plane with the surface of specimen 101. In some other embodiments, specimen positioning system is configured to rotate specimen 101 within a range of at least one degree about one or more axes of rotation aligned in-plane with the surface of specimen 101. In this manner, angle resolved measurements of specimen 101 are collected by metrology system 100 over any number of locations on the surface of specimen 101. In one example, computing system 130 communicates command signals to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 1, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 1. As depicted in FIG. 1, a rotation of specimen 101 about the z-axis is an in plane rotation of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions. For example, in one embodiment, a location of specimen 101 is measured over several angular increments within a range of −45 degrees to +45 degrees with respect to the normal orientation of specimen 101.

In general, specimen positioning system 140 may include any suitable combination of mechanical elements to achieve the desired linear and angular positioning performance, including, but not limited to goniometer stages, hexapod stages, angular stages, and linear stages.

In one aspect, metrology tool 100 includes a computing system configured to generate a free-form model of a material property of a measured structure and resolve an image of the measured structure by performing a fitting analysis of scatterometry measurement data with the model. The model that describes the geometry and material parameters of the structure under measurement is a free-form model that does not include a preconceived geometry and material distribution. In some embodiments, the model includes many small voxels (volumetric elements) that each have an independently adjustable material parameter value (e.g., electron density, absorptivity, or complex refractive index). In some other embodiments, the material properties are piecewise constant. The properties associated with each different material are determined a priori. The boundaries between different materials are free-form surfaces, and these surfaces can be determined by the level set algorithm.

By way of non-limiting example, the material property may be electron density, absorptivity, or complex index of refraction of the structure. However, in general, other material properties may be contemplated. In some embodiments, the measured structure is a device constructed on a wafer. In a preferred embodiment, the structure is spatially periodic in one or more directions aligned with the wafer surface. In some examples, the periodic structure is repeated in one dimension (e.g., x-direction) and extends uniformly in the other in-plane dimension (e.g., y-direction). In these examples, the free-form model is a two-dimensional model (i.e., area model). In these examples, area elements are employed to generate a two-dimensional image of the structure in the relevant directions (e.g., x-direction and z-direction). In these examples, the third dimension (e.g., y-direction) is uniform and redundant. In other examples, the periodic structure is repeated in an orthogonal or non-orthogonal pattern. In these examples, the free-form model is a three-dimensional model (i.e., volumetric model). In these examples, volume elements are employed to generate a three-dimensional image of the structure in the relevant directions (e.g., x-direction, y-direction, and z-direction). In some examples, the periodic structure is a dedicated metrology target placed in a scribe line between dies. In some other examples, the periodic structure is located in the active die area and is a part of a functional integrated circuit (e.g., memory, image sensor, logic device, etc.).

In the embodiment depicted in FIG. 1, computing system 130 is configured as model building and analysis engine 120 and is operable to implement model building and analysis functionality as described herein.

Figure 5:
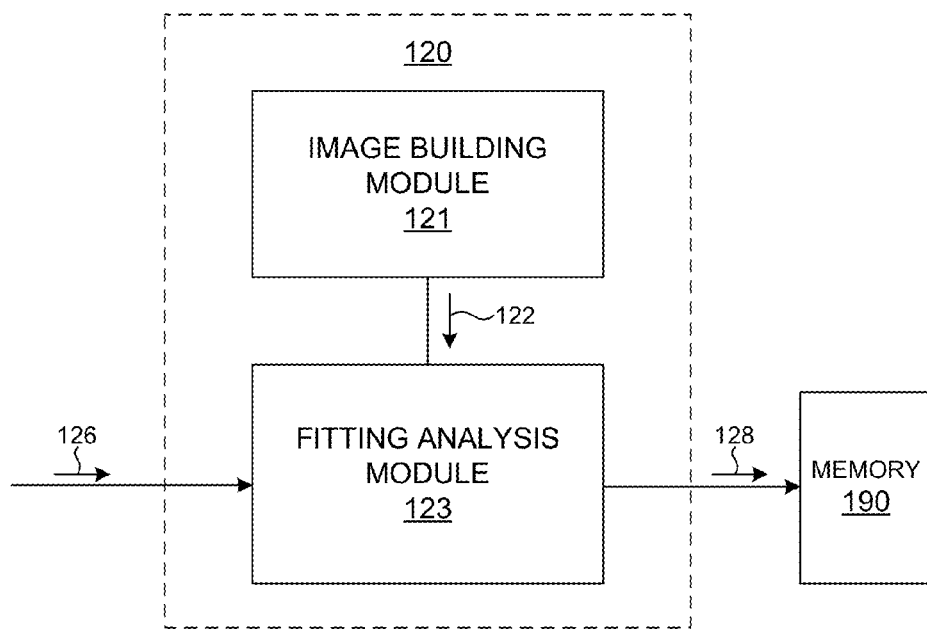
FIG. 5 is a diagram illustrative of a model building and analysis engine 120 configured to resolve a map of a material property of a measured specimen based on scatterometry measurement data in accordance with the methods described herein.

FIG. 5 is a diagram illustrative of model building and analysis engine 120 configured to resolve an image of a material property of a measured specimen based on scatterometry measurement data in accordance with the methods described herein. As depicted in FIG. 5, model building and analysis engine 120 includes an image building module 121 that generates an image 122 of a property of the measured structure.

Figure 6:
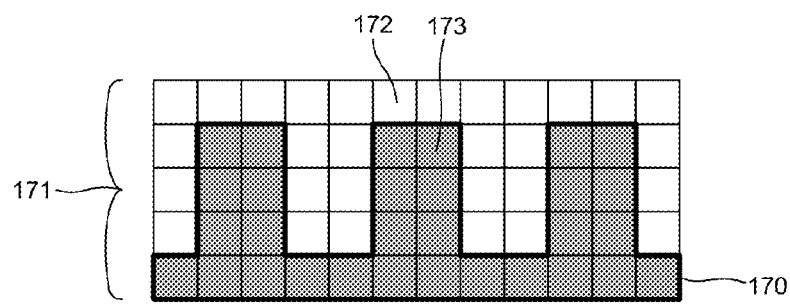
FIG. 6 is a diagram illustrative of a spatially discretized model of a semiconductor structure.

In one embodiment, image building module 121 generates a complex-valued map of the refractive index of the measured structure, $n(x,y,z)$. The complex refractive index corresponds to a particular electron density and a particular absorption cross-section. In one embodiment, the map of the complex refractive index is represented by complex numbers assigned to volume elements (voxels) representative of the measured structure. FIG. 6 depicts a periodic semiconductor structure 170 that is spatially discretized by a three dimensional array of voxels 171. Voxels 173 that correspond with the structure itself are shaded in FIG. 6. Voxels 172 that surround the structure 170 and may include different materials (e.g., air) are not shaded in FIG. 6. Each voxel is assigned an initial value for the expected complex index of refraction associated with the material within each voxel. In this example, image building module 121 generates a three dimensional image 122 of the complex index of refraction of the measured structure 170. In another embodiment, the map of the complex refractive index is represented by complex numbers assigned to area elements (pixels) representative of the measured structure. Each pixel is assigned an initial value for the expected complex index of refraction associated with the material within each pixel. In these examples, image building module 121 generates a two dimensional image of the complex index of refraction of the measured structure.

The voxels employed to describe the volume of the structure may be uniform, or may have irregular shapes and size. Furthermore, during the course of optimization, the shape of the voxels may be changed, e.g., subdivided or consolidated, so as to render the shape more realistic or to increase the speed of the optimization. When using non-uniform voxels, care must be taken to normalize functionals, such as the discrete spatial derivative, relative to the size or shape of the voxel. Similarly, pixels employed to describe the area of a structure (e.g., when the free-form model is two-dimensional) may be modified during optimization.

In some other embodiments, each map can be represented as a linear combination of pre-determined basis functions, the linear combination having complex coefficients. In another embodiment, the morphology of the specimen is optimized to fit the scatterometry data while taking advantage of properties of materials that are known to constitute the specimen. Each material boundary is represented by a level set $\{(x,y,z) | \phi(x,y,z)=0\}$ of a function, $\phi$, of position. The function $\phi(x,y,z)$ does not indicate any physical property of the specimen at the point (x,y,z). Its level set indicates the geometry of a material boundary. Material properties in the interior of the level set are assigned constant values that are measured or calculated a priori for bulk materials. The optimization algorithm makes iterative changes to function $\phi$ in order to fit the scatterometry data. The function $\phi$ can be represented by its samples on a mesh or by a linear combination of basis functions.

Although, a map of the complex index of refraction is described with reference to FIG. 6, a map of other material properties (e.g., electron density, absorptivity, etc.) may be contemplated.

The map 122 and the measured intensities of the diffraction orders 126 are received as input to fitting analysis module 123. In general, measurement signals 126 communicated to fitting analysis module 123 may include data associated with any combination of angle-resolved and wavelength-resolved SAXS measurements.

In a preferred embodiment the measured intensities are angle-resolved, i.e., the intensities of diffraction orders are measured for multiple values of m and n for many orientations of the wafer. In some embodiments, the wafer is held by a 6-axis stage that can translate and orient the wafer at the desired measurement positions with respect to the incoming beam. In some other embodiments, the wafer may be held fixed, or limited to a subset of the desired positions, and the direction of incidence of the beam of x-ray radiation is changed using moveable x-ray optics such as grazing incidence mirrors or a Fresnel zone-plate.

In another embodiment, the measured intensities are wavelength-resolved. In this embodiment, the polar angles of incidence, q and j, are held constant and measurements are taken for different wavelengths of the incident x-ray radiation. The wavelength can be changed by passing broadband light through an adjustable monochromator.

In the SAXS measurement, a periodic structure (e.g., structure 170) diffracts a collimated X-ray beam into diffraction orders. Each diffraction order travels in a particular, predictable direction. The angular spacing of the diffraction orders is inversely proportional to the lattice constant of the specimen divided by the wavelength. The diffraction orders can be individually detected by a detector array placed at some distance from the wafer. Each pixel of the detector outputs a signal that indicates the number of photons that hit the pixel. Outputs of pixels that belong to the same diffraction order are combined. The intensities of diffraction orders are of the form $I(m,n\ q,j,\lambda)$. $\{m,n\}$ are integer indices of diffraction orders. $\{q,j\}$ are azimuth and elevation angles of incidence beam (i.e., polar coordinates of the incident chief ray with respect to a coordinate system that is fixed to the wafer. $\lambda$ is the wavelength of the incident X-ray.

Fitting analysis module 123 receives the measurement signals 126 indicative of the measured intensities of the diffraction orders and refines the map 122 of the material property of the measured structure based on the measured data. In some examples, the fitting analysis is an iterative optimization that involves minimizing differences between the measured intensities of the diffraction orders and calculated intensities.

In this example, the intensities of the diffraction orders are calculated from the current estimate of the map of the refractive index using the first Born approximation. The approximation is described in greater detail in Principles of optics, Max Born and Emil Wolf, 7th Ed. Cambridge University Press, 1999, the subject matter of which is incorporated herein by reference it its entirety.

According to the Born-approximation, for an incident x-ray field, $u_{inc}$, the scattered X-ray field, $u_{sca}$, is a solution to the inhomogeneous Helmholtz equation as illustrated in equation (1).

$$\nabla^2 u_{sca} + k_0^2 u_{sca} = 2k_0^2(\alpha - i\beta)u_{inc}$$

$$k_0 = 2\pi/\lambda \qquad (1)$$

The position-dependent refractive index of the sample in complex notation is illustrated in equation (2).

$$\alpha(x,y,z) - i\beta(x,y,z) = 1 - n(x,y,z) \qquad (2)$$

For energies above approximately 10 keV, $\alpha$ and $\beta$ are simple functions of the classical electron radius, $r_e$, atomic photo-absorption cross section $\sigma_a$, the wavelength $\lambda$, atomic number Z, and the electron density $\rho$ as described in equations (3) and (4).

$$\alpha(x, y, z) = \frac{r_e \lambda^2}{2\pi} \rho(x, y, z) \qquad (3)$$

$$\beta(x, y, z) = \frac{\sigma_a \lambda}{4\pi Z} \rho(x, y, z) \qquad (4)$$

For a periodic, two-dimensional lattice pattern with a unit-cell of size ($\Delta x$, $\Delta y$), equation (5) expresses the refractive index as a Fourier series.

$$\alpha(x, y, z) - i\beta(x, y, z) = \sum_{m,n} c_{m,n}(z) \exp(iK_{m,n} \cdot (x, y)) \qquad (5)$$

$$K_{m,n} = \left( \frac{2\pi m}{\Lambda_x}, \frac{2\pi n}{\Lambda_y} \right)$$

Equation (1) is solved exactly using the Green's function for Helmholtz equation as expressed in equation (6).

$$u_{sca}(x, y, z) = \sum_{m,n} \exp(iq_{x,m}x + iq_{y,n}y + iq_{z,m,n}z) \frac{\hat{c}_{m,n}(\gamma_{m,n})}{iq_{z,m,n}} \qquad (6)$$

$$q_{x,m} = \frac{2\pi m}{\Lambda_x} + k_0 \sin\theta \cos\phi$$

$$q_{y,n} = \frac{2\pi n}{\Lambda_x} + k_0 \sin\theta \sin\phi$$

$$q_{z,m,n} = \sqrt{k_0^2 - q_{x,m}^2 - q_{y,n}^2}$$

$$\xi_{m,n} = \left(\frac{\lambda m}{\Lambda_x}\right)^2 + \left(\frac{\lambda n}{\Lambda_y}\right)^2 + 2\lambda \sin\theta \left( \frac{m\cos\phi}{\Lambda_x} + \frac{n\sin\phi}{\Lambda_y} \right)$$

$$\gamma_{m,n} = k_0 \frac{\xi_{m,n}}{\cos\theta + \sqrt{\cos\theta - \xi_{m,n}}}$$

$$\hat{c}_{m,n}(\gamma_{m,n}) \equiv \int c_{m,n}(z) \exp(i\gamma z) dz$$

The scattered field, $u_{sca}$, is a discrete sum of plane waves (diffraction orders). The intensity of the diffraction orders is $|\hat{c}_{m,n}(\gamma)|^2$.

Fitting analysis module 123 calculates the intensities of the diffraction orders from the current estimate of the map of the refractive index 122. At the first iteration, the intensities of the diffraction orders are calculated from the values of the refractive index of map 122. Module 123 generates a vector of differences between measured and calculated intensities of diffraction orders. Each entry of the difference vector pertains to a particular diffraction order m,n, a particular orientation of the wafer, and a particular wavelength. The current estimate of the map is refined in a way to reduce a norm of the difference vector using a non-linear minimization algorithm. In a preferred embodiment, the L2-norm is employed, however other norms may be contemplated (e.g., L1-norm, etc.).

A variety of non-linear, constrained, or a combination of non-linear and constrained optimization algorithms may be employed to iteratively refine the image. Preferred non-linear minimization algorithms include the Levenberg-Marquardt algorithm, Gauss-Newton algorithm, Sequential Quadratic Programming algorithm, and the quasi-Newton algorithm. Further details are described in Practical Optimization, Gill, Murray, and Wright, Emerald Publishing, 1982 and Numerical Methods for Unconstrained Optimization and Nonlinear Equations, Dennis and Schnabel, Soc. for Industrial & Applied Math., 1996, the subject matter of each is incorporated herein in its entirety. In some other embodiments, convex optimization such as convex and interior point methods may be employed. Further details are described in Convex Optimization, Boyd and Vandenberghe, Cambridge University Press, 2004, the subject matter of which is incorporated herein in its entirety.

To facilitate convergence of the optimization, a number of constraints may be introduced into the optimization. By way of non-limiting example, the optimization may be subject to any of the following constraints: the electron density cannot be negative, the absorption cannot be negative, the electron density and absorption cross-section have upper bounds for all materials, and the physical extent of the features under test have known upper and lower limits in the direction perpendicular to the wafer plane.

In another example, the absorption is ignored and the mapping is reduced to a mapping of electron density only. For many semiconductor materials, such as silicon or tungsten, the absorption coefficient, $\beta$, is an order of magnitude smaller than the scattering coefficient, a, at x-ray energies near or above 10 keV. Thus, the contribution of absorption to the measurement analysis can be safely ignored in many applications.

In a further aspect, the map is regularized by a norm of a functional of the complex refractive index. In some embodiments, the map is regularized by a norm of the value of the complex refractive index, its first derivative or its discrete counterpart, its second derivative or its discrete counterpart, or any combination of these. In one example, the total variation (i.e., the L1-norm) of the gradient of the complex refractive index is also included in the optimization cost function. In one example, the optimization cost function to be minimized with respect to n(x,y,z) includes the L2-norm of intensity difference and the total variation of the discrete gradient of n as illustrated in expression (7).

$$\sum_{m,n} \sum_{\theta,\varphi} \sum_{\lambda} [I_{MEASURED}(m, n, \theta, \varphi, \lambda) - I_{CALCULATED}(m, n, \theta, \varphi, \lambda)]^2 + \qquad (7)$$

$$\mu \sum_{x,y,z} \left[ \left| \frac{\partial n}{\partial x} \right| + \left| \frac{\partial n}{\partial y} \right| + \left| \frac{\partial n}{\partial z} \right| \right]$$

The amount of regularization is controlled by the non-negative factor $\mu$. In another example, the optimization cost function to be minimized with respect to n(x,y,z) includes a norm of the gradient of the complex index of refraction, and the optimization is subject to an upper bound on the value of a norm of the difference between the detected intensities of the diffraction orders and the estimated intensities of the diffraction orders.

In some other embodiments, a two-step optimization is employed. In one example, an optimization cost function that includes the L2-norm of differences between the measured and calculated intensities is minimized with respect to n(x,y,z) until a threshold error value is achieved. At this point, a different optimization cost function that includes a norm of the gradient of the complex refractive index is employed to further refine the image of the property (e.g., electron density) of the measured structure.

In some embodiments, two mixed norm optimizations are applied. In some examples, an L2-norm is applied to the intensity error (called a Fit measure) and an L1-norm is applied to a functional of the index of refraction (called an Entropy Measure). These examples are provided by way of illustration. Many other examples within the discipline of Compressed Sensing and/or Optimization Regularization may be contemplated. It is also contemplated that other techniques such as Akaike Information Criteria (AIC)/Bayesian Information Criteria (BIC), Ridge Regression, Basis Pursuit, Dantzig Selector, Rudin-Osher_Fatemi, Potts, Regularized Least Absolute Deviations (RLAD), SLOPE, and others may be applied.

Some examples have been provided that employ the L2 or L1 norms. However, it should be noted that any Lp norm, appropriate pseudo-norm such as the L0 norm, or statistical measure, such as Entropy or Kullbeck-Leibler divergence, may be applicable in the aforementioned examples.

In addition to Lp-norms, measures based on these norms, but modified to render them differentiable, such as the Huber or pseudo-Huber loss function, may also be applied. These techniques and others practiced in the field of robust regression are contemplated within the scope of this patent document.

After convergence of the iterative optimization, the refined map 128 of the property of the measured structure is stored in a memory 190.

In one further aspect, one or more parameters of interest, such as critical dimension (CD), sidewall angle (SWA), overlay, edge placement error, pitch walk, etc., are estimated directly from the resulting map. In some embodiments, the resulting map is rendered on a display device and a user is able to select a parameter of interest directly from the image. In response, computing system 130 is configured to determine the values of the selected parameter of interest. In some embodiments, the resulting map is analyzed automatically by computing system 130 to identify values of a parameter of interest directly from the image.

In another further aspect, metrology tool 100 includes a computing system configured to generate a structural model (e.g., geometric model, material model, or combined geometric and material model) of a measured structure of a specimen, generate a SAXS response model that includes at least one geometric parameter from the structural model, and resolve at least one specimen parameter value by performing a fitting analysis of SAXS measurement data with the SAXS response model. The analysis engine is used to compare the simulated SAXS signals with measured data thereby allowing the determination of geometric as well as material properties such as electron density and elemental identification and composition of the sample. In the embodiment depicted in FIG. 1, computing system 130 is configured as a model building and analysis engine configured to implement model building and analysis functionality as described herein.

Figure 7:
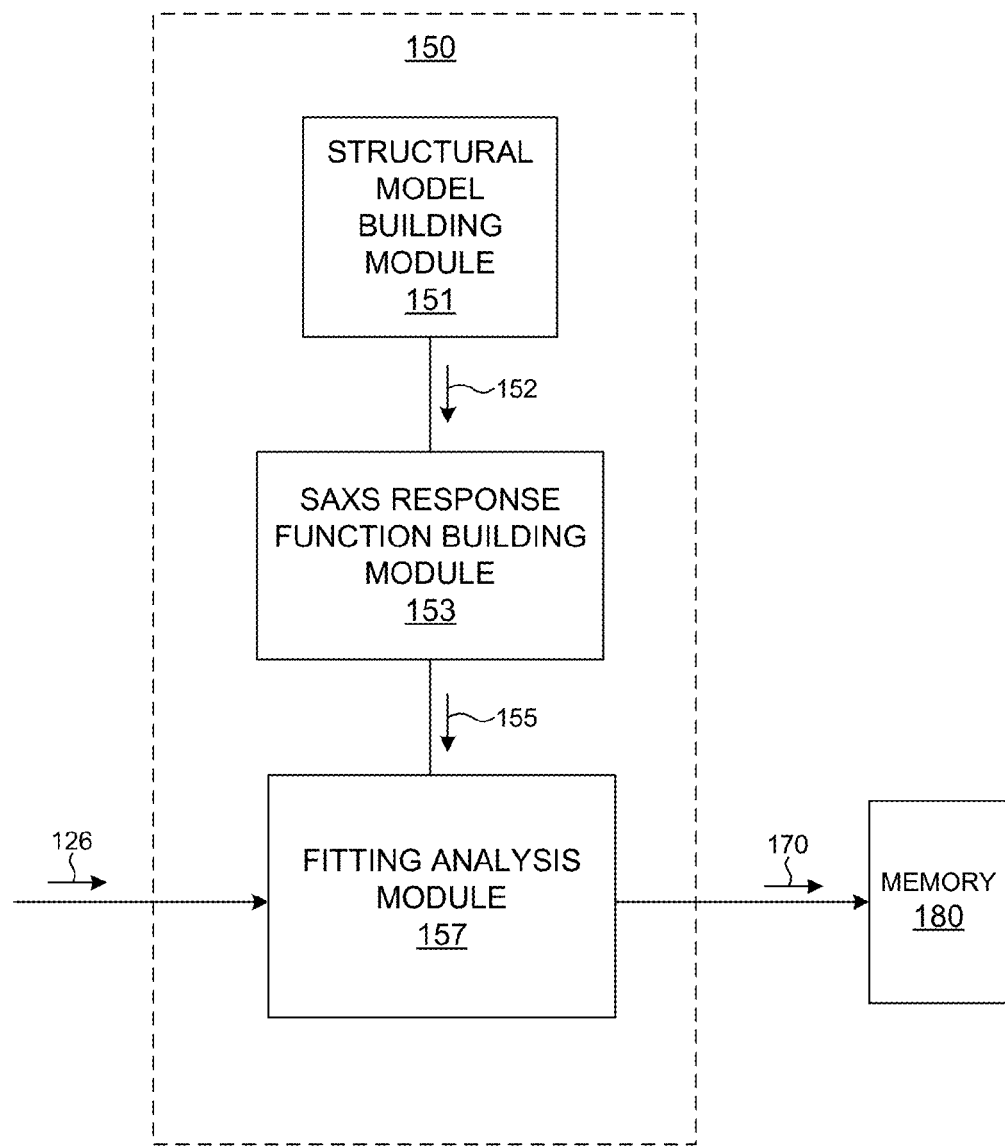
FIG. 7 is a diagram illustrative of a model building and analysis engine 150 configured to resolve specimen parameter values based on scatterometry measurement data in accordance with the methods described herein.

FIG. 7 is a diagram illustrative of an exemplary model building and analysis engine 150 implemented by computing system 130. As depicted in FIG. 7, model building and analysis engine 150 includes a structural model building module 151 that generates a structural model 152 of a measured structure of a specimen. In some embodiments, structural model 152 also includes material properties of the specimen. The structural model 152 is received as input to SAXS response function building module 153. SAXS response function building module 153 generates a SAXS response function model 155 based at least in part on the structural model 152. In some examples, the SAXS response function model 155 is based on x-ray form factors $$F(\vec{q}) = \int \rho(\vec{r}) e^{-i\vec{q}\cdot\vec{r}} d\vec{r} \qquad (8)$$

where F is the form factor, q is the scattering vector, and ρ(r) is the electron density of the specimen in spherical coordinates. The x-ray scattering intensity is then given by $$I(\vec{q}) = F^*F. \qquad (9)$$

SAXS response function model 155 is received as input to fitting analysis module 157. The fitting analysis module 157 compares the modeled SAXS response with the corresponding measured data to determine geometric as well as material properties of the specimen.

In some examples, the fitting of modeled data to experimental data is achieved by minimizing a chi-squared value. For example, for SAXS measurements, a chi-squared value can be defined as $$\chi^2_{SAXS} = \frac{1}{N_{SAXS}} \sum_j^{N_{SAXS}} \frac{\left(S_j^{SAXS\ model}(v_1, \ldots, v_L) - S_j^{SAXS\ experiment}\right)^2}{\sigma^2_{SAXS,j}} \qquad (10)$$

Where, $S_j^{SAXS\ experiment}$ is the measured SAXS signals 126 in the "channel" j, where the index j describes a set of system parameters such as diffraction order, energy, angular coordinate, etc. $S_j^{SAXS\ model}(V_1, \ldots, V_L)$ is the modeled SAXS signal $S_j$ for the "channel" j, evaluated for a set of structure (target) parameters $V_1, \ldots, V_L$, where these parameters describe geometric (CD, sidewall angle, overlay, etc.) and material (electron density, etc.). $\sigma_{SAXS,j}$ is the uncertainty associated with the jth channel. $N_{SAXS}$ is the total number of channels in the x-ray metrology. L is the number of parameters characterizing the metrology target.

Equation (10) assumes that the uncertainties associated with different channels are uncorrelated. In examples where the uncertainties associated with the different channels are correlated, a covariance between the uncertainties, can be calculated. In these examples a chi-squared value for SAXS measurements can be expressed as $$\chi^2_{SAXS} = \frac{1}{N_{SAXS}} \left(\vec{S}_j^{SAXS.\ model}(v_1, \ldots, v_M) - \vec{S}_j^{SAXS.\ experiment}\right)^T \qquad (11)$$

$$V_{SAXS}^{-1} \left(\vec{S}_j^{SAXS.\ model}(v_1, \ldots, v_M) - \vec{S}_j^{SAXS.\ experiment}\right)$$

where, $V_{SAXS}$ is the covariance matrix of the SAXS channel uncertainties, and T denotes the transpose.

In some examples, fitting analysis module 157 resolves at least one specimen parameter value by performing a fitting analysis on SAXS measurement data 126 with the SAXS response model 155. In some examples, $X_{SAXS}^2$ is optimized.

SAXS metrologies may contain more than one respective technology when calculating chi-squared values. For example, $X_{SAXS}^2$ may be calculated for the combined use of grazing incidence SAXS and transmission SAXS with a weight coefficient given to each technology.

As described hereinbefore, the fitting of SAXS data is achieved by minimization of chi-squared values. However, in general, the fitting of SAXS data may be achieved by other functions.

The fitting of SAXS metrology data is advantageous for any type of SAXS technology that provides sensitivity to geometric and/or material parameters of interest. Specimen parameters can be deterministic (e.g., CD, SWA, etc.) or statistical (e.g., rms height of sidewall roughness, roughness correlation length, etc.) as long as proper models describing SAXS beam interaction with the specimen are used.

Model building and analysis engine 150 improves the accuracy of measured parameters by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

In a further aspect, the precision and accuracy of SAXS measurements based on inversion of parametric models is improved based on a map of a material property (e.g., electron density) from the same SAXS data. The results of the parametric inversion are compared with the map and differences in the results are used to update the parameterization of the CD measurement model.

The distribution of the material property (e.g., index of refraction, electron density, etc.) may be used for a number of different purposes. By way of non-limiting example, the mapping may be used to 1) refine the parameterization of the physical model for model-based measurements such as SAXS or other model-based metrology solutions, 2) flag incidences that are not accurately described by the model in model-based metrology, 3) fix flagged values in a subsequent model-based measurement, 4) flag errors in target alignment in six degrees of freedom, 5) determine edge placement errors, 6) determine the overlay error within semiconductor layers, 7) determine the pitchwalk arising from multiple patterning, and 8) estimate the values of geometric properties of a structure such as critical dimension (CD), and sidewall angle (SWA).

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the SAXS detector 116 and the SAXS illumination optics 115 in any manner known in the art. For example, the one or more computing systems 130 may be coupled to computing systems associated with the SAXS detector 116 and the SAXS illumination optics 115, respectively. In another example, any of the SAXS detector 116 and the SAXS illumination optics 115 may be controlled directly by a single computer system coupled to computer system 130.

The computer system 130 may be configured to receive and/or acquire data or information from the subsystems of the system (e.g., SAXS detector 116 and SAXS illumination optics 115, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 126) from a storage medium (i.e., memory 132, 180, or 190) via a data link. For instance, spectral results obtained using a spectrometer of any of SAXS detector 116 may be stored in a permanent or semi-permanent memory device (e.g., memory 132, 180, or 190). In this regard, the measurement results may be imported from on-board memory or from an external memory system. Moreover, the computer system 130 may send data to other systems via a transmission medium. For instance, specimen parameter values 170 determined by computer system 130 may be stored in a permanent or semi-permanent memory device (e.g., memory 180). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some embodiments, a scatterometry analysis as described herein is implemented as part of a fabrication process tool. Examples of fabrication process tools include, but are not limited to, lithographic exposure tools, film deposition tools, implant tools, and etch tools. In this manner, the results of a SAXS analysis are used to control a fabrication process. In one example, SAXS measurement data collected from one or more targets is sent to a fabrication process tool. The SAXS measurement data is analyzed as described herein and the results used to adjust the operation of the fabrication process tool.

Scatterometry measurements as described herein may be used to determine characteristics of a variety of semiconductor structures. Exemplary structures include, but are not limited to, FinFETs, low-dimensional structures such as nanowires or graphene, sub 10 nm structures, lithographic structures, through substrate vias (TSVs), memory structures such as DRAM, DRAM 4F2, FLASH, MRAM and high aspect ratio memory structures. Exemplary structural characteristics include, but are not limited to, geometric parameters such as line edge roughness, line width roughness, pore size, pore density, side wall angle, profile, critical dimension, pitch, and material parameters such as electron density, composition, grain structure, morphology, stress, strain, and elemental identification.

Figure 8:
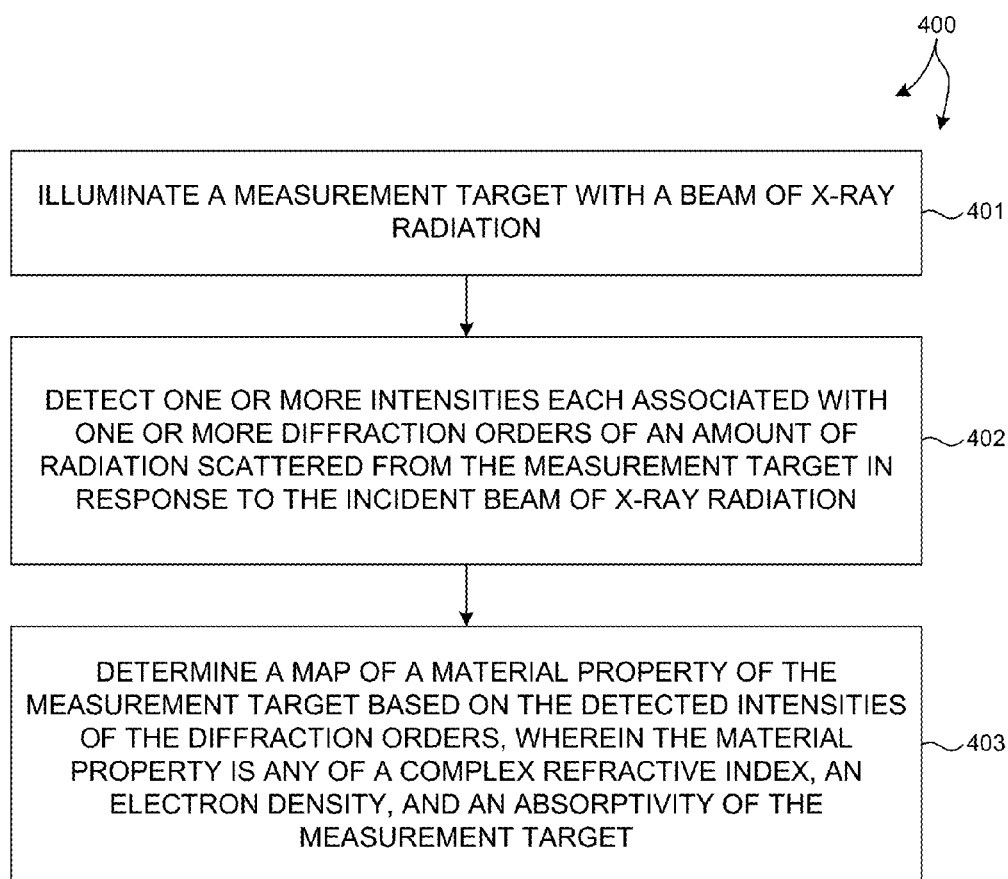
FIG. 8 is a flowchart illustrative of an exemplary method 400 of determining a map of a material property of a measured specimen based on scatterometry measurements.

FIG. 8 illustrates a method 400 suitable for implementation by the metrology system 100 of the present invention. In one aspect, it is recognized that data processing blocks of method 400 may be carried out via a pre-programmed algorithm executed by one or more processors of computing system 130. While the following description is presented in the context of metrology systems 100, 200, and 300, it is recognized herein that the particular structural aspects of metrology systems 100, 200, and 300 do not represent limitations and should be interpreted as illustrative only.

In block 401, a measurement target is illuminated with a beam of x-ray radiation.

In block 402, one or more intensities each associated with one or more diffraction orders of an amount of radiation scattered from the measurement target are detected in response to the incident beam of x-ray radiation.

In block 403, a map of a material property of the measurement target is determined based on the detected intensities of the diffraction orders. The material property is any of a complex refractive index, an electron density, and an absorptivity of the measurement target.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology systems described herein may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from imaging or structures under measurement.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, XRF disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
    illuminating a measurement target with a beam of x-ray radiation;
    detecting one or more intensities each associated with one or more diffraction orders of an amount of radiation scattered from the measurement target in response to the incident beam of x-ray radiation; and
    determining a map of a material property of the measurement target based on the detected intensities of the diffraction orders, wherein the material property is any of a complex refractive index, an electron density, and an absorptivity of the measurement target.

2. The method of claim 1, wherein the measurement target is a structure disposed on a planar substrate, wherein the structure is spatially periodic in at least one direction parallel to a planar surface of the planar substrate.

3. The method of claim 1, wherein the illuminating of the measurement target involves illuminating the measurement target with the beam of x-ray radiation at a plurality of angles of incidence with respect to the measurement target.

4. The method of claim 1, wherein the illuminating of the measurement target involves illuminating the measurement target with x-ray radiation at a plurality of different wavelengths.

5. The method of claim 1, wherein the determining the map of the material property of the measurement target involves a fitting analysis of the detected intensities of the diffraction orders with a free-form model that estimates values of the intensities of the diffraction orders based on an assumed map of the material property of the measurement target.

6. The method of claim 5, wherein the fitting analysis involves minimizing a difference between the detected intensities of the diffraction orders and the estimated intensities of the diffraction orders.

7. The method of claim 5, wherein the fitting analysis involves minimizing a functional of the material property of the measurement target.

8. The method of claim 7, wherein the fitting analysis involves minimizing a functional of the material property of the measurement target subject to an upper bound on a value of a difference between the detected intensities of the diffraction orders and the estimated intensities of the diffraction orders.

9. The method of claim 5, wherein the free-form model includes a plurality of volume elements representative of the measured target, and wherein the shape of at least one of the volume elements is changed during at least one iteration of the fitting analysis.

10. The method of claim 5, further comprising:
    determining at least one specimen parameter value associated with the measurement target based on a fitting analysis of the detected intensities of the diffraction orders with a geometrically parameterized response model; and
    modifying the geometrically parameterized response model of the measurement target based on a difference between the map of the material property of the measurement target and the at least one specimen parameter value.

11. The method of claim 5, further comprising:
    determining a value of a parameter of interest directly from the map of the material property of the measurement target.

12. A metrology system comprising:
    an x-ray illumination source configured to illuminate a measurement target with a beam of x-ray radiation;
    an x-ray detector configured to detect one or more intensities each associated with one or more diffraction orders of an amount of radiation scattered from the measurement target in response to the incident beam of x-ray radiation; and
    a computing system configured to
       determine a map of a material property of the measurement target based on the detected intensities of the diffraction orders, wherein the material property is any of a complex refractive index, an electron density, and an absorptivity of the measurement target.

13. The metrology system of claim 12, wherein the measurement target is a structure disposed on a planar substrate, wherein the structure is spatially periodic in at least one direction parallel to a planar surface of the planar substrate.

14. The metrology system of claim 12, wherein the x-ray illumination source illuminates the measurement target with the beam of x-ray radiation at a plurality of angles of incidence with respect to the measurement target.

15. The metrology system of claim 12, wherein the x-ray illumination source illuminates the measurement target with the beam of x-ray radiation at a plurality of different wavelengths.

16. The metrology system of claim 12, wherein the computing system determines the map of the material property of the measurement target based on a fitting analysis of the detected intensities of the diffraction orders with a free-form model that estimates values of the intensities of the diffraction orders based on an assumed map of the material property of the measurement target.

17. The metrology system of claim 16, wherein the fitting analysis is based at least in part on minimizing a difference between the detected intensities of the diffraction orders and the estimated intensities of the diffraction orders.

18. The metrology system of claim 16, wherein the fitting analysis is based at least in part on minimizing a functional of the material property of the measurement target.

19. The metrology system of claim 18, wherein the fitting analysis is based at least in part on minimizing a functional of the material property of the measurement target subject to an upper bound on a value of a difference between the detected intensities of the diffraction orders and the estimated intensities of the diffraction orders.

20. The metrology system of claim 16, wherein the free-form model includes a plurality of volume elements representative of the measured target, and wherein the shape of at least one of the volume elements is changed during at least one iteration of the fitting analysis.

21. The metrology system of claim 16, wherein the computing system is further configured to:
  determine at least one specimen parameter value associated with the measurement target based on a fitting analysis of the detected intensities of the diffraction orders with a geometrically parameterized response model; and
  modify the geometrically parameterized response model of the measurement target based on a difference between the map of the material property of the measurement target and the at least one specimen parameter value.

22. The metrology system of claim 16, wherein the computing system is further configured to:
  determine a value of a parameter of interest directly from the map of the material property of the measurement target.

23. A non-transitory, computer-readable medium, comprising:
  code for causing a computer to determine a map of a material property of a measurement target based on detected intensities of diffraction orders, wherein the material property is any of a complex refractive index, an electron density, and an absorptivity of the measurement target, wherein the detected intensities are each associated with one or more diffraction orders of radiation scattered from the measurement target in response to an incident beam of x-ray radiation.

24. The non-transitory, computer-readable medium of claim 23, further comprising:
  code for causing the computer to determine the map of the material property of the measurement target based on a fitting analysis of the detected intensities of the diffraction orders with a free-form model that estimates values of the intensities of the diffraction orders based on an assumed map of the material property of the measurement target.

25. The non-transitory, computer-readable medium of claim 24, further comprising:
  code for causing the computer to determine a value of a parameter of interest directly from the map of the material property of the measurement target.

* * * * *